United States Patent [19]
Tsao

[11] 3,968,200
[45] July 6, 1976

[54] REACTOR EFFLUENT QUENCH SYSTEM

[75] Inventor: Utah Tsao, Jersey City, N.J.

[73] Assignee: The Lummus Company, Bloomfield, N.J.

[22] Filed: Mar. 27, 1972

[21] Appl. No.: 238,196

[52] U.S. Cl. .............................. 423/488; 423/472; 423/481; 423/493; 423/502
[51] Int. Cl.² ...................... C01B 7/08; C01G 3/04; C01G 3/06
[58] Field of Search .......... 423/488, 472, 493, 502, 423/500, 481

[56] References Cited
UNITED STATES PATENTS

| | | | |
|---|---|---|---|
| 2,047,611 | 7/1936 | Baxter | 423/488 X |
| 2,382,788 | 8/1945 | Gorin | 423/488 |
| 2,436,432 | 2/1948 | Hunter | 423/488 |
| 2,542,961 | 2/1951 | Johnson et al. | 423/502 |
| 2,547,928 | 4/1951 | Davis et al. | 423/502 |
| 2,644,846 | 7/1953 | Johnson et al. | 423/507 X |
| 2,665,240 | 1/1954 | Brumbaugh | 423/488 |
| 3,360,483 | 12/1967 | Diamond et al. | 423/502 X |
| 3,460,903 | 8/1969 | Holemann et al. | 423/493 |
| 3,667,913 | 6/1972 | Hund | 423/502 |
| 3,669,650 | 6/1972 | Elstein et al. | 423/472 |
| 3,682,592 | 8/1972 | Kovacs | 423/488 |
| 3,816,599 | 6/1974 | Kafes | 423/488 |

FOREIGN PATENTS OR APPLICATIONS

788,421 1/1958 United Kingdom ................. 423/488

Primary Examiner—Edward Stern
Attorney, Agent, or Firm—Marn & Jangarathis

[57] ABSTRACT

Process for recovering hydrogen chloride from an aqueous hydrogen chloride off-gas from an oxychlorination reaction wherein hydrogen chloride is separated from the off-gas as an aqueous solution of hydrogen chloride and employed as feed to an oxychlorination reaction. The process is particularly applicable to the production of vinyl chloride.

12 Claims, 2 Drawing Figures

REACTOR EFFLUENT QUENCH SYSTEM

This invention relates to hydrogen chloride recovery. More particularly, this invention relates to the recovery of hydrogen chloride from the off-gas from an oxychlorination. This invention further relates to the recovery of hydrogen chloride in the production of vinyl chloride.

Oxychlorination reactions using hydrogen chloride and oxygen are well known in the art. One type of oxychlorination reaction involves contacting a mixture of a multivalent metal chloride in both its higher and lower valence state such as a mixture of cuprous and cupric chloride, either as an unsupported melt or supported on a suitable support, with hydrogen chloride and a molecular oxygen-containing gas to increase the content of the higher valent metal chloride; e.g., cupric chloride. Representative examples of such processes are disclosed in U.S. Pat. No. 2,418,931; U.S. Pat. No. 2,407,828; U.S. Pat. No. 3,546,016; Canadian Pat. No. 705,925; and Canadian Pat. No. 711,287.

Another type of oxychlorination reaction involves contacting hydrogen chloride and oxygen with a hydrocarbon or chlorinated hydrocarbon generally in the presence of a suitable catalyst, to produce chlorinated hydrocarbons, as disclosed for example, in U.S. Pat. No. 3,256,352 and British Pat. No. 998,689.

In most cases, the hydrogen chloride introduced into the oxychlorination is not completely reacted, and in such cases, the overall economics of the process may be dependent upon the effective recovery of any unreacted hydrogen chloride. The effluent from the oxychlorination reaction includes, in addition to unreacted hydrogen chloride, water vapor, as reaction product. Water and hydrogen chloride form an azeotrope which presents some difficulties in effectively and economically recovering such hydrogen chloride.

Similarly in the production of vinyl chloride, as disclosed in U.S. application Ser. No. 153,374 filed on June 15, 1971 and assigned to the same assignee, and U.S. application Ser. No. 157,496 and now U.S. Pat. No. 3,879,482, there are off-gases which include both water vapor and hydrogen chloride, and economics may require effective recovery of such hydrogen chloride.

Accordingly, an object of this invention is to provide for improved recovery of hydrogen chloride.

Another object of this invention is to provide for recovery of hydrogen chloride from an aqueous hydrogen chloride off-gas from an oxychlorination reaction.

A further object of this invention is to provide for recovery of hydrogen chloride from an aqueous hydrogen chloride off-gas generated in the production of vinyl chloride.

These and other objects of the invention should be readily apparent from reading the following detailed description of the invention with reference to the accompanying drawings wherein.

The objects of this invention are broadly accomplished, in one aspect, by recovering an aqueous solution of hydrogen chloride from an oxychlorination reaction effluent and passing recovered aqueous hydrogen chloride to an oxychlorination reaction as a portion of the reaction feed. In this manner, the hydrogen chloride present in the effluent from an oxychlorination reaction is effectively and economically utilized to produce desired reaction product.

More particularly, an aqueous hydrogen chloride containing gaseous effluent from an oxychlorination reaction is initially quenched with a partially vaporizing quench of aqueous hydrogen chloride which cools the effluent and results in a remaining quench liquid having an increased concentration of hydrogen chloride. The remaining aqueous hydrogen chloride quench liquid is recycled to the oxychlorination reactor. The effluent containing the aqueous hydrogen chloride withdrawn from the oxychlorination reaction, and the vaporized portion of the aqueous hydrogen chloride quench liquid, is then further cooled to condense aqueous hydrogen chloride therefrom, with condensed aqueous hydrogen chloride being recycled as quench liquid for cooling of the oxychlorination reaction effluent.

In accordance with a preferred embodiment of the invention, the concentration of the aqueous hydrogen chloride liquid condensed from the effluent is carefully controlled to reduce the amount of water recycled to the oxychlorination reaction, without simultaneously causing an unacceptable loss of hydrogen chloride in the off-gas from the oxychlorination reaction. In accordance with the present invention, the hydrogen chloride concentration of the aqueous hydrogen chloride condensed from the oxychlorination reaction effluent is preferably controlled at from about 8 to about 20 percent, and more preferably from about 8 to about 16 percent, all by weight, in that, at such concentrations, the amount of water recycled to the oxychlorinator is reduced without also resulting in an unacceptable loss of hydrogen chloride in the off-gas. It is to be understood that at increasing hydrogen chloride concentrations in the condensed aqueous hydrogen chloride, there is an increasing concentration of hydrogen chloride in the off-gas, but the condensation of less concentrated aqueous hydrogen chloride results in an increase in the amount of water recycled to the oxychlorination reaction. The condensation of aqueous hydrogen chloride within the hereinabove specified ranges has been found to provide particularly good results.

The oxychlorination reactions to which the present invention is applicable are of several types and include: (1) reaction between molecular oxygen, hydrogen chloride and a salt mixture of the higher and lower valent forms of a multivalent metal chloride to enrich the high valent metal chloride content of the mixture; (2) reaction between molecular oxygen, hydrogen chloride and a hydrocarbon or a partially chlorinated hydrocarbon, generally a lower (1–4 carbon atoms) aliphatic hydrocarbon or partially chlorinated lower aliphatic hydrocarbon to produce a chlorinated hydrocarbon; (3) reaction between hydrogen chloride and oxygen to produce chlorine, (generally referred to as a Deacon reaction, but for the purposes of this invention this reaction is considered an oxychlorination); (4) reaction between an oxychloride of a multivalent metal and hydrogen chloride to produce the higher valent metal chloride; and (5) reaction between an oxychloride of a multivalent metal, hydrogen chloride and a hydrocarbon or partially chlorinated hydrocarbon to produce a chlorinated hydrocarbon. These reactions all result in the production of a reaction effluent which includes water as reaction product, and which also includes hydrogen chloride as unreacted feed; therefore, the teachings of the present invention are applicable to such reactions. These reactions are known in the art, and are represented by the following equations:

$$2HCl + \tfrac{1}{2} O_2 + 2CuCl \rightarrow 2CuCl_2 + H_2O \qquad (1)$$

$$C_2H_4 + \tfrac{1}{2} O_2 + HCl \rightarrow C_2H_3Cl + H_2O \qquad (2)$$

$$2HCl + \tfrac{1}{2} O_2 \rightarrow Cl_2 + H_2O \qquad (3)$$

$$CuO\cdot CuCl_2 + 2HCl \rightarrow 2CuCl_2 + H_2O \qquad (4)$$

$$CuO\cdot CuCl_2 + HCl + C_2H_4 \rightarrow C_2H_3Cl + H_2O + 2CuCl \qquad (5)$$

The reactions represented by equations (2) and (3) are effected in the presence of a suitable catalyst; i.e., a Deacon or oxychlorination type catalyst, generally a chloride of a multivalent metal; i.e., a metal having more than one positive valence state, such as the chlorides of iron, manganese, copper, cobalt or chromium, preferably copper. These metal chlorides may be used alone or may be combined with other components. The reaction conditions and catalysts which are used in such oxychlorination reactions are known in the art and, therefore, no further explanation thereof is deemed necessary for a full understanding of the present invention. In general, the reaction temperature is from about 500°F. to about 1200°F.

Figure 1:
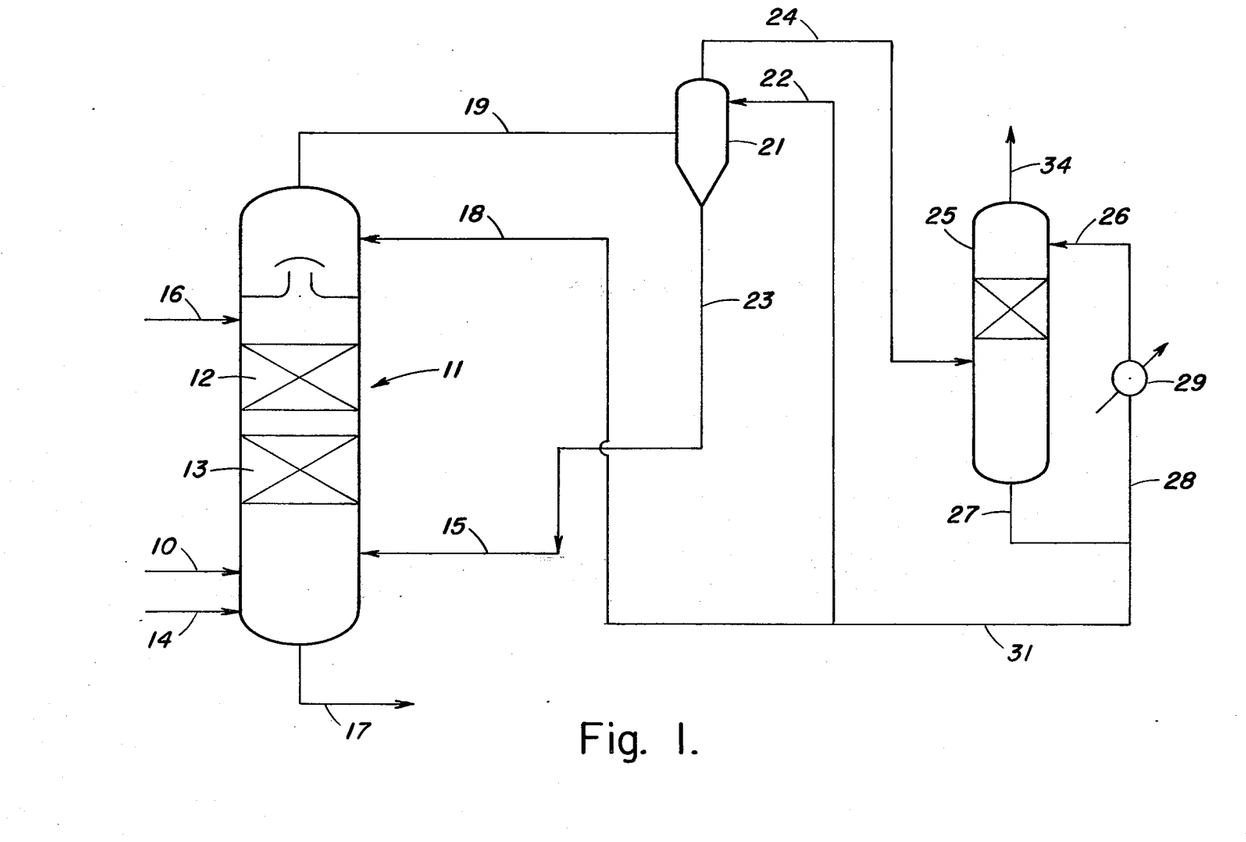
FIG. 1 is a simplified schematic flow diagram of an embodiment of the invention.

The process of the invention will be further described with respect to an embodiment thereof illustrated in FIG. 1 of the drawings, but it is to be understood that the scope of the invention is not to be limited thereby.

Referring to FIG. 1 of the drawings, a hydrogen chloride containing gas in line 10 is introduced into a salt oxychlorination reactor 11, containing packed sections 12 and 13 to increase vapor-liquid contact. An oxygen-containing gas, such as air, is introduced into reactor 11 through line 14. An aqueous liquid solution of hydrogen chloride, obtained as hereinafter described, is introduced into reactor 11 through line 15.

A molten salt mixture of, for example, cuprous and cupric chloride, and also potassium chloride, as a melting point depressant, is introduced into the top of reactor 11 through line 16 and countercurrently contacts the ascending gas, resulting in oxychlorination to enrich the content of cupric chloride in the melt. The reactor 11 is operated as known in the art, generally at a temperature from about 600°F to about 900°F., and at a pressure from about 1–10 atm. A cupric chloride-enriched melt is withdrawn from the bottom of reactor 11 through line 17 for use in subsequent processing steps, as known in the art. The water introduced with the aqueous hydrogen chloride is vaporized in reactor 11 and withdrawn with the off-gas therefrom.

An off-gas, containing unreacted hydrogen chloride, water vapor, any components introduced with the hydrogen chloride and components of the molecular oxygen-containing gas, such as nitrogen and unreacted oxygen, if any, is contacted in the top of reactor 11 with a spray of quench liquid introduced through line 18 to cool the off-gas and condense and separate any entrained molten salt. As a result of such contact the quench liquid is vaporized. The effluent gas is cooled to a temperature at which the molten salt is still in the form of a melt to permit the molten salt to flow back into the reactor 11.

The cooled gaseous stream withdrawn from reactor 11 through line 19 is introduced into quench vessel 21 wherein the gaseous stream is directly contacted with an aqueous hydrogen chloride stream introduced therein through line 22. The quenching in vessel 21 is effected in a manner such that the aqueous hydrogen chloride quench liquid introduced through line 22 is partially vaporized which produces a remaining aqueous hydrogen chloride quench liquid having a higher concentration of hydrogen chloride. The quenching in vessel 21 also functions to separate any remaining entrained salt from the gaseous effluent. In accordance with a preferred embodiment, quenching in vessel 21 is effected in a manner to cool the effluent to a temperature from about 220°F. to about 250°F.

The remaining liquid aqueous hydrogen chloride quench liquid, containing any remaining salt, is withdrawn from vessel 21 through line 23 and introduced, as recycle feed, into reactor 11 through line 15.

The effluent gas, now also containing vaporized quench liquid, withdrawn from vessel 21 through line 24 is introduced into a direct contact quench tower 25, of a type known in the art, wherein the gas is cooled by direct contact with aqueous hydrogen chloride quench liquid introduced through line 26. The quenching in tower 25 is controlled in a manner such that not all of the hydrogen chloride present in the off-gas is recovered therefrom in that such complete recovery would be accompanied by an unacceptable corresponding amount of water condensation. In accordance with the present invention, as hereinabove noted, condensation is preferably recovered to provide a condensed aqueous hydrogen chloride solution having a hydrogen chloride concentration from about 8 to about 20 percent, preferably from about 8 to about 16 percent, all by weight. In general, such a result can be achieved by effecting cooling in tower 25 to a temperature from about 140°F to about 160°F.; i.e., the gas withdrawn from the tower is at the specified temperature.

The off-gas withdrawn from tower 25 still contains some hydrogen chloride, and may be further treated, if required, to remove such remaining hydrogen chloride prior to release to the atmosphere.

An aqueous hydrogen chloride solution is withdrawn from tower 25 through line 27 and a first portion thereof passed through line 28, including a suitable cooler 29, for introduction into the quench tower 25 to meet the cooling requirements therefore. A second portion of the aqueous hydrogen chloride in line 31 is passed through lines 18 and 22 to meet the quenching requirements of reactor 11 and of vessel 21, respectively.

It should be readily apparent that in accordance with the present invention hydrogen chloride which is present in the off-gas from an oxychlorination reaction is economically recovered therefrom for recycle to the oxychlorination reaction, while simultaneously eliminating the necessity to provide separate means for recovering the salt used as a catalyst and/or reactant in the process.

It should be readily apparent that numerous modifications and variations of the hereinabove described embodiment are possible within the scope and spirit of the invention. Thus, for example, although the invention has been particularly described with respect to the use of direct contact cooling, other cooling means may be employed, such as, for example, an indirect heat exchanger in combination with a vapor-liquid separator.

It should also be apparent that although the embodiment has been particularly described with respect to the preferred use of multivalent metal chloride as an unsupported molten mixture, the present invention is also applicable to those processes which utilize supported multivalent metal halides, as known in the art; e.g., as disclosed in U.S. Pat. Nos. 2,418,931 and 2,407,828.

It should further be apparent that salt oxychlorination, including the hydrogen chloride recovery of the present invention, may be utilized in any of a wide variety of processes requiring such salt oxychlorination, such as, for example, the processes disclosed in U.S. Pat. Nos. 2,418,931; 2,407,828; 3,548,016; Canadian Pat. No. 705,925 and Canadian Pat. No. 711,287.

Similarly, the hydrogen chloride recovery process of the invention is equally applicable to those processes in which a hydrocarbon or chlorinated hydrocarbon is oxychlorinated with hydrogen chloride and molecular oxygen; e.g., as disclosed in British Pat. No. 998,689; British Pat. No. 934,329; U.S. Pat. No. 3,256,352; and U.S. Pat. No. 3,557,229.

The hydrogen chloride gas used as the net feed to the oxychlorination reactor may be either a fresh hydrogen chloride feed or a recycle hydrogen chloride obtained from another reactor employed in an overall process. It should also be apparent that the hydrogen chloride gas introduced into the oxychlorinator may contain other components, such as carbon oxides, chlorine, water vapor; e.g., the hydrogen chloride gas may be a combustion effluent as disclosed, for example, in U.S. Pat. No. 3,548,016 in which case the off-gas from the oxychlorinator will contain other components, such as carbon oxides.

The teachings of the present invention are particularly applicable to a process for producing vinyl chloride from ethane and/or ethylene. More particularly, ethane and/or ethylene and chlorine and/or hydrogen chloride, are contacted with a molten mixture including a multivalent metal chloride in both its higher and lower valence state and the oxychloride of the metal, to produce a chlorination reaction effluent which includes vinyl chloride, dichloroethane, water vapor and generally also some hydrogen chloride. The hydrogen chloride is present as a result of equilibrium requirements. The dichloroethane reaction product is generally a mixture of 1,2-dichloroethane and 1,1-dichloroethane, primarily 1,2-dichloroethane, but it is to be understood that in some cases, the dichloroethane could be comprised of essentially only 1,2-dichloroethane. As hereinafter employed, dichloroethane generically refers to 1,2-dichloroethane and/or 1,1-dichloroethane. The chlorination reaction effluent is introduced into a separation and recovery zone wherein vinyl chloride is recovered as product. The dichloroethane is either recovered as co-reaction product or recovered and dehydrochlorinated to vinyl chloride. An aqueous solution of hydrogen chloride is also recovered from the chlorination effluent. The salt mixture is then contacted with molecular oxygen and recovered aqueous hydrogen chloride to both produce the oxychloride of the multivalent metal, and recover the hydrogen chloride by enriching the salt in the higher valent metal chloride. The salt mixture is then circulated to the vinyl chloride production step.

The chloride of a multivalent metal; i.e., a metal having more than one positive valence state, is generally a mixture of the higher and lower valent chlorides of either manganese, iron, copper, cobalt or chromium, preferably copper. If the mixture is to be employed as a melt, the mixture may also include a metal salt melting point depressant which is non-volatile and resistant to oxygen at the process conditions, such as a chloride of a univalent metal; i.e., a metal having only one positive valence state, to provide a salt mixture having a reduced melting point. The univalent metal chlorides are preferably alkali metal chlorides, such as potassium and lithium chloride, in particular, but it is to be understood that other metal chlorides and mixtures thereof, such as the heavy metal chlorides; i.e., heavier than copper, of Groups I, II, III and IV of the Periodic Table; e.g., zinc, silver and thallium chloride, may also be employed. A preferred composition is formed from copper chlorides and potassium chloride, with the potassium chloride comprising from about 20 to about 40 percent, by weight, of the composition, with the remainder being copper chlorides.

The dichloroethanes (primarily 1,2-dichloroethane and generally also varying amounts of 1,1-dichloroethane) generated during the chloroination is recovered as product or dehydrochlorinated to vinyl chloride at dehydrochlorination temperatures and pressures. The dehydrochlorination may be effected in any of a wide variety of ways. Thus, for example, the dichloroethane may be introduced into a dehydrochlorination zone, of a type known in the art, and thermally or catalytically dehydrochlorinated to vinyl chloride. Alternatively, the dichloroethane may be be recovered and dehydrochlorinated by introducing the dichloroethane into the chloroination reaction zone. As a further alternative, the dichloroethane may be recovered and dehydrochlorinated by contacting thereof with a molten mixture of a multivalent metal chloride in both its higher and lower valence state. As still another alternative, the dichloroethane may be dehydrochlorinated by contact with a molten mixture which comprises cupric chloride, cuprous chloride and copper oxychloride, in which case the hydrogen chloride reacts with the oxychloride and the effluent contains water vapor and equilibrium amounts of hydrogen chloride. In such a case, the present invention may also be employed to recover such hydrogen chloride.

The chlorination reaction for producing vinyl chloride from ethane and/or ethylene may be effected at temperatures from about 700°F to about 1200°F and at pressures from about 1 to about 20 atmospheres. The chlorination reaction is preferably effected at temperatures from about 750°F to about 1000°F and more preferably from about 800°F to about 900°F in that such temperature conditions, in combination with the other processing conditions, have been found to provide improved yields of vinyl chloride. The contacting of the feed and salt mixture is generally effected in a countercurrent fashion, preferably with the feed as a continuous vapor phase, at residence times from about 1 to about 60 seconds, although longer residence times may be employed.

The contacting of the salt mixture with molecular oxygen and the aqueous hydrogen chloride is generally effected at temperatures from about 600°F to about 900°F., although higher temperatures may be employed. The preferred operating temperatures for the oxidation of the salt mixture and recovery of hydrogen chloride from the aqueous hydrogen chloride solution are from about 750°F to about 870°F.

The use of the hydrogen chloride recovery process of the present invention in a process for producing vinyl chloride will be described in more detail with respect to a preferred embodiment illustrated in FIG. 2 of the drawings.

Figure 2:
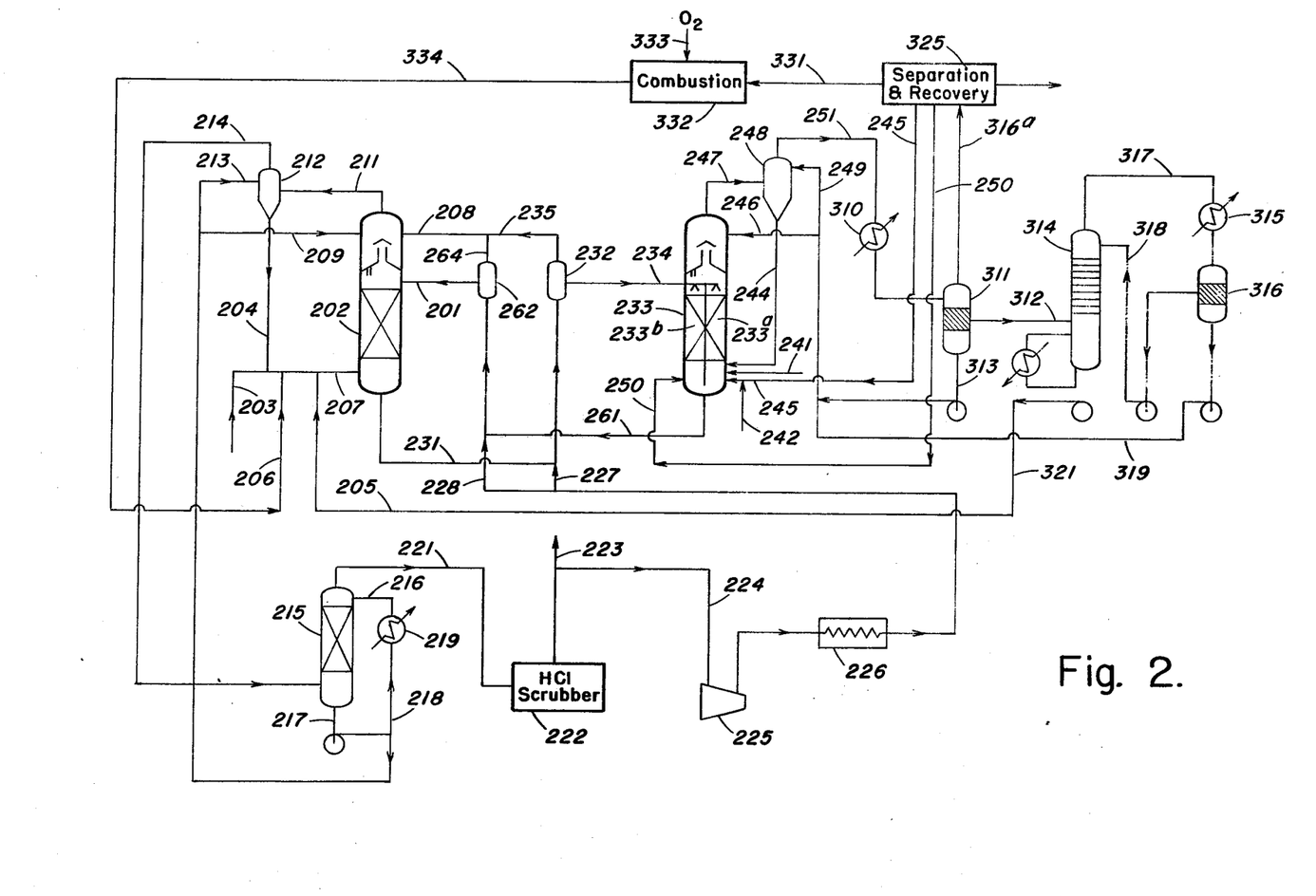
FIG. 2 is a simplified schematic flow diagram of an embodiment of a vinyl chloride production process incorporating the present invention.

Referring now to FIG. 2, a molten chloride salt, such as a mixture of potassium chloride, cupric and cuprous chloride in line 201 is introduced into the top of an oxidation vessel 202, maintained at a pressure from about 1 to about 20 atm. A compressed oxygen-containing gas, such as air, in line 203, an aqueous solution of hydrogen chloride in lines 204 and 205, obtained as hereinafter described, and a by-product combustion effluent, in line 206, comprising chlorine and/or hydrogen chloride, as well as carbon oxides, water vapor, nitrogen and perhaps unreacted oxygen, obtained as hereinafter described, are combined in line 207 and introduced into reactor 202. As a result of the countercurrent contact between the feed introduced through line 207 and the descending molten salt mixture, the salt is oxidized to produce copper oxychloride, and the hydrogen chloride and/or chlorine introduced with the combustion effluent and the hydrogen chloride introduced as aqueous hydrogen chloride are absorbed by the molten salt to produce cupric chloride. In addition, the water introduced with the aqueous hydrogen chloride is vaporized.

An effluent gas, including water vapor, nitrogen, carbon oxides and unabsorbed hydrogen chloride rises into the top of vessel 202 wherein the effluent gas is combined with lift gas, as hereinafter described, introduced through line 208. The combined gas is directly contacted in the top of vessel 202 with a spray of aqueous hydrogen chloride quench liquid introduced through line 209 to cool the combined gas and eliminate any vaporized and entrained salts therefrom. The effluent gas is cooled to a temperature at which the molten salt is still in the form of a melt to permit the molten salt to flow back into the reactor 202.

The cooled gaseous stream withdrawn from reactor 202 through line 211 is introduced into quench vessel 212 wherein the gaseous stream is directly contacted with an aqueous hydrogen chloride stream introduced therein through line 213. The quenching in vessel 211 is effected in a manner such that the aqueous hydrogen chloride quench liquid introduced through line 213 is partially vaporized which produces a remaining aqueous hydrogen chloride quench liquid having a higher concentration of hydrogen chloride. The quenching in vessel 212 also functions to separate any remaining entrained salt from the gaseous effluent. In accordance with a preferred embodiment, quenching in vessel 212 is effected in a manner to cool the effluent to a temperature from about 220°F to about 250°F.

The remaining liquid aqueous hydrogen chloride quench liquid, containing any remaining salt, is withdrawn from vessel 212 through line 204 and introduced, as recycle feed, into reactor 202.

The effluent gas, now also containing vaporized quench liquid, withdrawn from vessel 212 through line 214 is introduced into a direct contact quench tower 215, of a type known in the art, wherein the gas is cooled by direct contact with aqueous hydrogen chloride quench liquid introduced through line 216. The quenching in tower 215 is controlled in a manner such that not all of the hydrogen chloride present in the off-gas is recovered therefrom in that such complete recovery would be accompanied by an unacceptable corresponding amount of water condensation. In accordance with the present invention, as hereinabove noted, condensation is preferably controlled to provide a condensed aqueous hydrogen chloride solution having a hydrogen chloride concentration from about 8 to about 20 percent, preferably from about 8 to about 16 percent, all by weight. In general such a result can be achieved by effecting cooling in tower 215 to a temperature from about 140°F to about 160°F.

An aqueous hydrogen chloride solution is withdrawn from tower 215 through line 217 and a first portion thereof passed through line 218, including a suitable cooler 219, for introduction into the quench tower 215 to meet the cooling requirements therefor. A second portion of the aqueous hydrogen chloride is passed through lines 209 and 213 to meet the quenching requirements of reactor 202 and of vessel 212, respectively.

The gas withdrawn from tower 215 through line 221 is caustic and water-washed in zone 222 to remove remaining hydrogen chloride, and a portion thereof released to the atmosphere through line 223. The remaining portion of the gas in line 224 is compressed in compressor 225 and the temperature thereof regulated in heat exchanger 226 prior to passage through lines 227 and 228 for use as lift gas for transporting molten salt, as hereinafter described.

The molten salt, now containing copper oxychloride, is withdrawn from the bottom of vessel 202 through line 231 and lifted by the lift gas in line 227 into a separation vessel 232 positioned adjacent the top of the reaction portion of a chlorination vessel 233. In separator 232, the molten salt is separated from the lift gas, with the molten salt being introduced into the top of the reaction portion of chlorination vessel 233 through line 234. The lift gas is withdrawn from vessel 232 through 235, and combined with lift gas used for transporting salt to the oxidation reactor 202 for introduction into the quenching portion of vessel 211 through line 208 to thereby separate any entrained and vaporized salt therefrom.

The reaction vessel 233 is divided into two reaction sections 233a and 233b, with reaction section 233a functioning as a chlorination section and section 233b as a dehydrochlorination section. The molten salt in line 234 is introduced into both sections 233a and 233b.

Fresh feed chlorine and/or hydrogen chloride is introduced into the bottom of section 233a through line 241, and fresh feed ethane and/or ethylene, preferably ethane, is introduced in line 242 and is combined with a recycle stream comprised of ethyl chloride, ethane and ethylene in line 245 for introduction into the bottom of reaction section 233a. A liquid chlorinated hydrocarbon stream obtained as hereinafter described, is also introduced into section 233a through line 244.

The reaction section 233a is operated at the temperatures and pressures hereinabove described to effect chlorination, dehydrogenation and dehydrochlorination of the fresh feed and recycle in direct countercurrent contact of the feed and recycle with the descending molten salt.

Recycle dichloroethane, preferably 1,2-dichloroethane, in line 250 is introduced into reaction section 233b and is countercurrently contacted with the molten salt to effect dehydrochlorination thereof to vinyl chloride.

The effluents from each of the sections 233a and 233b, each containing equilibrium amounts of hydrogen chloride, are combined in the top portion of reactor 233.

An effluent gas, containing vinyl chloride, ethyl chloride, dichloroethane, other chlorinated hydrocarbons (one or more of the following: dichloroethylenes, trichloroethylene, tetrachloroethylene, trichloroethane and tetrachloroethane) ethane, ethylene, water vapor and some hydrogen chloride, (the major portion of the hydrogen chloride produced from dichloroethane reacts with the oxychloride of the salt) rises into the top of the vessel 233 wherein the effluent gas is directly contacted with a spray of quench liquid, in particular one or more of the chlorinated hydrocarbons produced in reactor 233, introduced through line 246 to cool the effluent gas and thereby eliminate any vaporized and entrained salts therefrom. The effluent gas is cooled to a temperature at which the salt mixture remains in molten form to permit the molten salt to flow back into the reactor 233.

The effluent gas, now containing vaporized quench liquid is withdrawn from vessel 233 through line 247 and introduced into a quench vessel 248 wherein the effluent gas is contacted with chlorinated hydrocarbon quench liquid in line 249 to further cool the gas and separate any remaining entrained salts. The gas is cooled to a temperature at which essentially no aqueous hydrogen chloride is condensed therefrom. Any chlorinated hydrocarbon condensed in vessel 248 is recycled to reactor 233 through line 244. The effluent gas is withdrawn from vessel 248 through line 251 and treated as hereinafter described.

A molten salt is withdrawn from the bottom of reactor 233 through line 261 and lifted by lift gas in line 228 into a separation vessel 262 positioned adjacent the top of reactor 211. In separator 262, the molten salt is separated from the lift gas, and introduced through line 201 into vessel 202. The lift gas is withdrawn from separator 262 through line 264 and combined with the lift gas in line 235 for introduction into the top quenching section of vessel 202 through line 208.

The reaction effluent in line 251 is cooled in condenser 310, primarily to condense a portion of the water vapor and thereby recover hydrogen chloride as an aqueous hydrogen chloride solution; the aforesaid cooling also resulting in the condensation of chlorinated hydrocarbons, including the chlorinated hydrocarbons used as quench liquid. The cooling in condenser 310 is effected to provide, as disclosed with respect to the hydrogen chloride recovery from oxidizer 202, a condensed aqueous hydrogen chloride solution having a hydrogen chloride concentration from about 8 to about 20 percent, and preferably from about 8 to about 16 percent, all by weight. The condensed water and chlorinated hydrocarbons are separated in a separator 311, with a water phase being withdrawn through line 312. The chlorinated hydrocarbons in line 313 are recycled through lines 246 and 249 as quench liquid for reactor 233 and quench vessel 248, respectively. The water phase comprised of aqueous hydrogen chloride in line 312 is stripped of entrained and dissolved chlorinated hydrocarbon in a stripping column 314, of a type known in the art, including an overhead condenser 315 and reflux drum 316. The overhead withdrawn from stripper 314 through line 317 is condensed in condenser 315 and introduced into drum 316. Any water withdrawn with the overhead is separated in drum 316 and recycled to stripper 314 through line 318. The chlorinated hydrocarbons are recovered in line 319 and combined with the chlorinated hydrocarbons in line 313. Alternatively, the oil stripper 314 could also be employed to effect some concentration of the aqueous hydrogen chloride by removing from the system a portion of the water condensed from the overhead. The separated water should be treated to remove any dissolved chlorinated hydrocarbons for pollution control.

The aqueous hydrogen chloride recovered as bottoms from column 314 in line 321 is introduced into reactor 202 through line 205 for recovery of hydrogen chloride as hereinabove described.

The remainder of the gaseous effluent from vessel 311 in line 316 is then introduced into a separation and recovery section, schematically indicated as 325 to recover the various components therefrom. The separation and recovery section is described in more detail in copending application Ser. No. 153,374, filed June 15, 1971.

Vinyl chloride is recovered as reaction product from separation and recovery section 325. Ethane, ethylene and ethylchloride recovered in separation and recovery section 325 are recycled to reactor 233 through line 245 for ultimate conversion to vinyl chloride. Dichloroethane preferably only 1,2-dichloroethane, produced in chlorination section 233a is recovered in separation and recovery section 325 and recycled through line 250 to section 233b.

Other chlorinated hydrocarbons comprised of one or more of the following chlorinated hydrocarbons: dichloroethylenes, trichloroethylene, tetrachloroethylene, trichloroethanes and tetrachloroethanes recovered in separation and recovery section 325 in line 331 are introduced into a combustion chamber schematically indicated as 332 along with air in line 333, and a combustion effluent including hydrogen chloride, chlorine, carbon oxides, water vapor and nitrogen, and optionally oxygen, is withdrawn from the combustion chamber through line 334 for introduction into reactor 202 through line 206 as hereinabove described. The details of this recovery are described in application Ser. No. 95,030, filed Dec. 4, 1970 and now U.S. Pat. No. 3,879,481, which is hereby incorporated by reference.

It should be readily apparent that in accordance with the hereinabove described embodiment essentially all chlorine values introduced into the system are recovered for ultimate conversion to vinyl chloride.

Thus, for example, although the hydrogen chloride recovery of the present invention has been particularly described with respect to the production of vinyl chloride in a system employing two reactors, the teachings of the invention are equally applicable to the other embodiments for producing vinyl chloride described in application Ser. No. 153,374 which is hereby incorporated by reference. Thus, for example, as described in application Ser. No. 153,374 the chlorination and dehydrochlorination could be effected in a single zone. Similarly, separate reactors could be used for effecting the dehydrochlorination and chlorination reactions.

It is also to be understood that the teachings of the present invention are also applicable to the recovery of hydrogen chloride in the production of chlorinated hydrocarbons other than vinyl chloride by the use of molten salts, such as, chlorinated methanes, chlorinated benzene, etc. It is further to be understood that the teachings of the present invention are also applicable to the use of molten salts for the production of compounds other than chlorinated hydrocarbons.

The invention will be further described with respect to the following example which further illustrates the invention. It is to be understood, however, that the scope of the invention is not to be limited thereby.

EXAMPLE

An off-gas in line 211 at a temperature of 430°F (the off-gas is previously cooled to 430°F from a temperature of 855°F. by quench liquid in line 209) containing 2 percent, by weight, hydrogen chloride is contacted in vessel 212 with a 10 percent, by weight, aqueous hydrogen chloride solution at a temperature of 210°F to effect cooling of the gas to 230°F. A 17 percent, by weight, aqueous hydrogen chloride solution is recycled to vessel 202 through line 204.

The gas in line 214 is passed to tower 215 which is operated at conditions to provide a 10 percent, by weight, hydrogen chloride solution in line 217; i.e., the overhead vapor withdrawn in line 221 is at a temperature of 145°F, and the liquid in line 217 is at a temperature of 210°F.

The hydrogen chloride recovery, based on hydrogen chloride in line 211, is 98.5 percent, with 1.5 percent of the hydrogen chloride originally present in the gas in line 211 being withdrawn through line 221.

An off-gas in line 247, containing 0.2 percent, by weight, hydrogen chloride is cooled in vessel 248 and cooler 310 to a temperature of 185°F to produce a 10 percent, by weight, aqueous hydrogen chloride solution. The 10 percent, by weight, aqueous hydrogen chloride solution, after stripping of chlorinated hydrocarbons therefrom, is passed to the oxidizer through line 205.

The hydrogen chloride recovery, based on hydrogen chloride in line 247, is 96 percent, with the remainder of the hydrogen chloride being neutralized in the separation and recovery system.

The process of the present invention is advantageous in that hydrogen chloride is effectively recovered from an oxychlorination off-gas without the necessity of a costly and difficult azeotropic separation of hydrogen chloride and water. The process is particularly advantageous in the recovery of hydrogen chloride from an off-gas generated in a vinyl chloride process in that such recovery is facilely integrated into the overall process.

Numerous modifications and variations of the present invention are possible in light of the above teachings and, therefore, within the scope of the appended claims the invention may be practiced other than as described.

What is claimed is:

1. In an oxychlorination reaction, a process for recovering hydrogen chloride, comprising:
    withdrawing a gas containing hydrogen chloride and water vapor from an oxychlorination reaction zone;
    contacting said gas in a first quench zone with an aqueous hydrogen chloride quench liquid to cool said gas, said contacting partially vaporizing said quench liquid to produce a remaining aqueous hydrogen chloride liquid having a hydrogen chloride concentration greater than the hydrogen chloride concentration of said quench liquid;
    introducing said remaining aqueous hydrogen chloride liquid into said oxychlorination reaction zone;
    further cooling cooled gas from said first quench zone in a second quench zone to produce aqueous hydrogen chloride having a hydrogen chloride concentration from about 8 to about 20 percent, by weight; and
    passing aqueous hydrogen chloride from said second quench zone to said first quench zone as said aqueous hydrogen chloride quench liquid.

2. The process of claim 1 wherein said second quench zone is a direct contact quench zone and said further cooling is effected by direct contact with aqueous hydrogen chloride.

3. The process of claim 2 wherein the gas is cooled in said direct contact quench zone to a temperature from about 220°F. to about 250°F.

4. The process of claim 3 wherein said cooled gas is further cooled to a temperature from about 140°F. to about 160°F.

5. In the oxidation of a molten salt, a process for recovering hydrogen chloride, comprising:
    contacting in a reaction zone a molten salt mixture comprising a multivalent metal chloride in its higher and lower valence states with gaseous molecular oxygen, gaseous hydrogen chloride and an aqueous solution of hydrogen chloride to produce the oxychloride of the multivalent metal and to recover hydrogen chloride by enriching the higher valent metal chloride content of the molten mixture;
    withdrawing a gas containing hydrogen chloride and water vapor from the reaction zone;
    contacting said gas in a first quench zone with an aqueous hydrogen chloride quench liquid to cool said gas, said contacting partially vaporizing said quench liquid to produce a remaining aqueous hydrogen chloride liquid having a hydrogen chloride concentration greater than the hydrogen chloride concentration of said quench liquid;
    introducing said remaining aqueous hydrogen chloride liquid into said reaction zone as said aqueous hydrogen chloride;
    further cooling cooled gas from said first quench zone in a second quench zone to produce aqueous hydrogen chloride having a hydrogen chloride concentration from about 8 to about 20 percent, by weight; and
    passing aqueous hydrogen chloride from said second quench zone to said first quench zone as said aqueous hydrogen chloride quench liquid.

6. The process of claim 5 wherein the gas is cooled in said second quench zone to a temperature from about 220°F. to about 250°F.

7. The process of claim 6 wherein said cooled gas is further cooled to a temperature from about 140°F. to about 160°F.

8. The process of claim 7 wherein said multivalent metal chloride is copper chloride.

9. The process of claim 1 wherein a portion of the aqueous hydrogen chloride from the second quench zone is employed to directly cool the gas containing hydrogen chloride and water vapor prior to the first quench zone, resulting in complete vaporization of said portion of the aqueous hydrogen chloride from the second quench zone.

10. The process of claim 5 wherein a portion of the aqueous hydrogen chloride from the second quench zone is employed to directly cool the gas containing hydrogen chloride and water vapor prior to the first quench zone, resulting in complete vaporization of said portion of the aqueous hydrogen chloride from the second quench zone.

11. The process of claim 1 wherein said aqueous hydrogen chloride has a hydrogen chloride concentration from about 8 to about 16 percent, by weight.

12. The process of claim 5 wherein said aqueous hydrogen chloride has a hydrogen chloride concentration from about 8 to about 16 percent, by weight.

* * * * *

UNITED STATES PATENT OFFICE
CERTIFICATE OF CORRECTION

Patent No. 3,968,200                    Dated July 6, 1976

Inventor(s) Utah Tsao

It is certified that error appears in the above-identified patent and that said Letters Patent are hereby corrected as shown below:

Column 6, line 22, "chloroination" should be -- chlorination --;

line 31, delete "be", second occurence;

line 33, "chloroination" should be -- chlorination --.

Column 8, line 38, after "through", insert -- line --;

Line 61, delete "in" and insert -- by --.

Signed and Sealed this

*Twenty-seventh* Day of *December 1977*

[SEAL]

*Attest:*

RUTH C. MASON
*Attesting Officer*

LUTRELLE F. PARKER
*Acting Commissioner of Patents and Trademarks*